(12) United States Patent
Kim et al.

(10) Patent No.: US 12,012,499 B2
(45) Date of Patent: Jun. 18, 2024

(54) CYCLOHEXANE TRIESTER-BASED PLASTICIZER COMPOSITION AND RESIN COMPOSITION INCLUDING THE SAME

(71) Applicant: LG CHEM, LTD., Seoul (KR)

(72) Inventors: Hyun Kyu Kim, Daejeon (KR); Jeong Ju Moon, Daejeon (KR); Woo Hyuk Choi, Daejeon (KR); Joo Ho Kim, Daejeon (KR)

(73) Assignee: LG Chem, Ltd., Seoul (KR)

( * ) Notice: Subject to any disclaimer, the term of this patent is extended or adjusted under 35 U.S.C. 154(b) by 523 days.

(21) Appl. No.: 17/442,435

(22) PCT Filed: Apr. 29, 2020

(86) PCT No.: PCT/KR2020/005689
§ 371 (c)(1),
(2) Date: Sep. 23, 2021

(87) PCT Pub. No.: WO2020/222536
PCT Pub. Date: Nov. 5, 2020

(65) Prior Publication Data
US 2022/0185988 A1    Jun. 16, 2022

(30) Foreign Application Priority Data
May 2, 2019   (KR) .................. 10-2019-0051716

(51) Int. Cl.
*C08K 5/12* (2006.01)
*C07C 69/75* (2006.01)

(52) U.S. Cl.
CPC ................ *C08K 5/12* (2013.01); *C07C 69/75* (2013.01); *C07C 2601/08* (2017.05); *C07C 2601/14* (2017.05)

(58) Field of Classification Search
CPC ........ C08K 5/12; C07C 69/75; C07C 2601/08
See application file for complete search history.

(56) References Cited

U.S. PATENT DOCUMENTS

| | | | |
|---|---|---|---|
| 7,208,545 B1 | 4/2007 | Brunner et al. | |
| 2002/0019559 A1 | 2/2002 | Brunner et al. | |
| 2005/0106405 A1* | 5/2005 | Breitscheidel | C08K 5/12 428/522 |
| 2011/0053065 A1 | 3/2011 | Wu et al. | |
| 2011/0232825 A1* | 9/2011 | Mack | C09K 3/10 524/285 |
| 2011/0281987 A1 | 11/2011 | Godwin et al. | |
| 2012/0138206 A1 | 6/2012 | Wagner et al. | |
| 2015/0246867 A1 | 9/2015 | Castiglioni et al. | |
| 2017/0015810 A1 | 1/2017 | Miyazaki et al. | |
| 2017/0088691 A1 | 3/2017 | Woldt et al. | |
| 2018/0319954 A1 | 11/2018 | Woldt et al. | |

FOREIGN PATENT DOCUMENTS

| | | |
|---|---|---|
| CN | 102239198 B | 1/2015 |
| EP | 2 810 932 A1 | 12/2014 |
| JP | 2015-212014 A | 11/2015 |
| KR | 10-0635396 B | 10/2006 |
| KR | 10-2008-0082169 A | 9/2008 |
| KR | 10-2016-0139001 A | 12/2016 |
| WO | 99/32427 A1 | 7/1999 |
| WO | 2014053535 A2 | 4/2014 |
| WO | 2017/169730 A1 | 10/2017 |

* cited by examiner

*Primary Examiner* — Doris L Lee
(74) *Attorney, Agent, or Firm* — Bryan Cave Leighton Paisner LLP

(57) ABSTRACT

The present disclosure relates to a plasticizer composition characterized in having alkyl groups derived from an isomer mixture of hexyl alcohol with the degree of branching of less than 2.0 as a cyclohexane triester. When the plasticizer composition is applied to a resin, stress resistance and mechanical properties may be maintained to equal or better levels, migration and loss properties and plasticization efficiency may keep balance, and light resistance and heat resistance may be markedly improved.

10 Claims, No Drawings

CYCLOHEXANE TRIESTER-BASED PLASTICIZER COMPOSITION AND RESIN COMPOSITION INCLUDING THE SAME

CROSS-REFERENCE TO RELATED APPLICATIONS

The present application is a National Phase entry pursuant to 35 U.S.C. § 371 of International Application No. PCT/KR2020/005689, filed on Apr. 29, 2020, and claims the benefit of and priority to Korean Patent Application No. 10-2019-0051716, filed on May 2, 2019, all of which are hereby incorporated by reference in their entirety for all purposes as if fully set forth herein.

TECHNICAL FIELD

The present invention relates to a cyclohexane triester-based plasticizer composition including cyclohexane triester in which the carbon numbers of the alkyl radicals of the components in the composition are the same, and a resin composition including the same.

BACKGROUND ART

Generally, plasticizers are obtained through the reaction of alcohols with polycarboxylic acids such as phthalic acid and adipic acid to form corresponding esters. In addition, considering the internal and external regulations on harmful phthalate-based plasticizers to the human body, studies are being continued on plasticizer compositions which may replace phthalate-based plasticizers such as terephthalate-based, adipate-based and other polymer-based plasticizers.

Meanwhile, regardless of the type of industry including plastisol type of industry of flooring materials, wallpaper, soft and hard sheets, etc., calendaring type of industry, or extrusion/injection compound type of industry, the demand for eco-friendly products is increasing. In order to reinforce the quality properties, processability and productivity by the finished products, an appropriate plasticizer is required considering discoloration, migration, mechanical properties, etc.

According to the properties required by the types of industry in various areas of usage, such as tensile strength, elongation rate, light resistance, migration, gelling properties and absorption rate, supplementary materials such as a plasticizer, a filler, a stabilizer, a viscosity decreasing agent, a dispersant, a defoaming agent and a foaming agent are mixed with a PVC resin.

For example, in case of applying di(2-ethylhexyl) terephthalate (DEHTP) which is relatively cheap and widely used among plasticizer compositions which may be applied to PVC, hardness or sol viscosity is high, absorption rate of a plasticizer is relatively slow, and migration and stress migration are not good.

As improvements on the above limitations, the application of a transesterification product with butanol as a plasticizer, as a composition including DEHTP may be considered. In this case, plasticization efficiency is improved but volatile loss or thermal stability is inferior and mechanical properties are somewhat degraded, and the improvement of physical properties is required. Accordingly, there is no solution but employing a method compensating the defects through mixing with a second plasticizer at the present time.

However, in case of applying the second plasticizer, there are drawbacks of generating unexpected defects as follows: the change of the physical properties is hard to predict, the application may become a factor of increasing the unit cost of the product, the improvement of the physical properties is not clearly shown except for specific cases, and problems relating to compatibility with a resin may arise.

In addition, if a material like tri(2-ethylhexyl) trimellitate or triisononyl trimellitate is applied as a trimellitate-based product in order to improve the inferior migration and loss properties of the DEHTP products, migration or loss properties may be improved, but plasticization efficiency may be degraded, and a great deal of the material is required to be injected to provide a resin with suitable plasticization effect, and considering relatively the high unit price of the products, commercialization thereof is impossible.

Accordingly, the development of products for solving the environmental issues of the conventional phthalate-based products or products for improving inferior physical properties of the eco-friendly products for improving the environmental issues of the phthalate-based products is required.

DISCLOSURE OF THE INVENTION

Technical Problem

An object of the present invention is to provide a plasticizer composition securing suitable absorption rate, maintaining and improving equal or better levels of mechanical properties and stress resistance when compared with the conventional plasticizer, and at the same time, having suitable balance between migration and loss properties and plasticization efficiency, and markedly improving light resistance, by including cyclohexane triesters in which isomer radicals are combined, wherein the carbon numbers of the alkyl radicals of components are the same.

Technical Solution

To solve the tasks, there is provided in the present invention, a cyclohexane triester-based plasticizer composition including a cyclohexane triester-based composition including one or more cyclohexane triesters of Formula 1, wherein an alkyl group of the cyclohexane triester is derived from an isomer mixture of hexyl alcohol having a degree of branching of 2.0 or less, and the isomer mixture of hexyl alcohol comprises two or more selected from the group consisting of 1-hexanol, 1-methylpentanol, 2-methylpentanol, 3-methylpentanol, 4-methylpentanol, 1,1-dimethylbutanol, 1,2-dimethylbutanol, 1,3-dimethylbutanol, 2,2-dimethylbutanol, 2,3-dimethylbutanol, 3,3-dimethylbutanol, 1-ethylbutanol, 2-ethylbutanol, 3-ethylbutanol and cyclopentyl methanol:

[Formula 1]

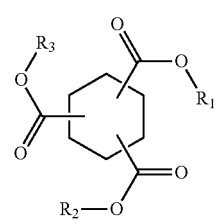

In Formula 1,
$R_1$ to $R_3$ are each independently an n-hexyl group, a branch type hexyl group or a cyclopentylmethyl group.

In order to solve the tasks, there is provided in the present invention, a resin composition including 100 parts by weight of a resin and 5 to 150 parts by weight of the plasticizer composition.

Advantageous Effects

The plasticizer composition of the present invention, if used in a resin composition, has suitable level of absorption rate and excellent processability and maintains and improves to equal or better level of mechanical properties and stress resistance when compared with the conventional plasticizer, and at the same time, has suitable balance between migration, loss properties and plasticization efficiency and markedly improved light resistance.

MODE FOR CARRYING OUT THE INVENTION

It will be understood that terms or words used in the present disclosure and claims should not be interpreted as having a meaning that is defined in common or in dictionaries, however should be interpreted in consistent with the technical scope of the present invention based on the principle that inventors may appropriately define the concept of the terms to explain the invention at his best method.

Definition of Terms

The term "composition" as used in the present disclosure includes a mixture of materials including the corresponding composition as well as a reaction product and a decomposition product formed from the materials of the corresponding composition.

The term "straight vinyl chloride polymer" as used in the present disclosure may be one type of vinyl chloride polymers and polymerized by suspension polymerization, bulk polymerization, etc., and may refer to a polymer having a porous particle shape in which a large number of pores having a size of tens to hundreds of micrometers, no cohesiveness, and excellent flowability are dispersed.

The term "paste vinyl chloride polymer" as used in the present disclosure may be one type of vinyl chloride polymers and polymerized by microsuspension polymerization, microseed polymerization, emulsion polymerization, etc., and may refer to a polymer having minute particles without pores and a size of tens to thousands of nanometers, cohesiveness, and inferior flowability.

The terms "comprising", and "having" and the derivatives thereof in the present invention, though these terms are particularly disclosed or not, do not intended to preclude the presence of optional additional components, steps, or processes. In order to avoid any uncertainty, all compositions claimed by using the term "comprising" may include optional additional additives, auxiliaries, or compounds, including a polymer or any other materials, unless otherwise described to the contrary. In contrast, the term "consisting essentially of ~" excludes unnecessary ones for operation and precludes optional other components, steps or processes from the scope of optional continuous description. The term "consisting of ~" precludes optional components, steps or processes, which are not particularly described or illustrated.

Measurement Methods

In the present disclosure, the content analysis of the components in a composition is conducted by gas chromatography measurement using a gas chromatography equipment of Agilent Co. (product name: Agilent 7890 GC, column: HP-5, carrier gas: helium (flow rate of 2.4 ml/min), detector: F.I.D., injection volume: 1 μl, initial value: 70° C./4.2 min, end value: 280° C./7.8 min, program rate: 15° C./min).

In the present disclosure, "hardness" means Shore hardness (Shore "A" and/or Shore "D") at 25° C. and is measured in conditions of 3T 10s using ASTM D2240. The hardness may be an index for evaluating plasticization efficiency, and the lower the value is, the better the plasticization efficiency is.

In the present disclosure, "tensile strength" is obtained according to an ASTM D638 method by drawing a specimen in a cross head speed of 200 mm/min (1T) using a test apparatus of U.T.M (manufacturer: Instron, model name: 4466), measuring a point where the specimen is cut, and calculating according to the following Mathematical Formula 1:

Tensile strength (kgf/cm$^2$)=load value (kgf)/thickness (cm)×width (cm)    [Mathematical Formula 1]

In the present disclosure, "elongation rate" is obtained according to an ASTM D638 method by drawing a specimen in a cross head speed of 200 mm/min (1T) using the U.T.M, measuring a point where the specimen is cut, and calculating according to the following Mathematical Formula 2:

Elongation rate(%)=length after elongation/initial length×100    [Mathematical Formula 2]

In the present disclosure, "migration loss" is obtained according to KSM-3156, by which a specimen with a thickness of 2 mm or more is obtained, glass plates are attached onto both sides of the specimen and a load of 1 kgf/cm$^2$ is applied. The specimen is stood in a hot air circulation type oven (80° C.) for 72 hours, then taken out therefrom and cooled at room temperature for 4 hours. Then, the glass plates attached onto both sides of the specimen are removed, the weights before and after standing the glass plates and the specimen plate in the oven are measured, and the migration loss is calculated according to Mathematical Formula 3 below.

Migration loss(%)={[(weight of initial specimen)−(weight of specimen after standing in oven)]/(weight of initial specimen)}×100    [Mathematical Formula 3]

In the present disclosure, "volatile loss" is obtained by processing a specimen at 80° C. for 72 hours and then, measuring the weight of the specimen.

Volatile loss (wt %)={[(weight of initial specimen)−(weight of specimen after processing)]/(weight of initial specimen)}×100    [Mathematical Formula 4]

In case of the various measurement conditions, the details of the conditions of the temperature, the speed of revolution, the time, etc., may be somewhat changed according to situations, and if the conditions are different, a measurement method and its conditions are required to be separately indicated.

Hereinafter, the present invention will be explained in more detail to assist the understanding of the present invention.

According to an embodiment of the present invention, a plasticizer composition is a cyclohexane triester and includes a cyclohexane triester-based plasticizer composition including one or more cyclohexane triesters of the following Formula 1, wherein alkyl groups of the cyclohexane triester are derived from an isomer mixture of hexyl alcohol having a degree of branching of 2.0 or less:

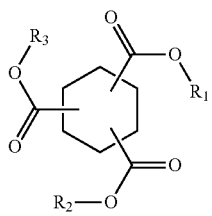

[Formula 1]

In Formula 1, $R_1$ to $R_3$ are each independently an n-hexyl group, a branch type hexyl group or a cyclopentyl methyl group.

According to an embodiment of the present invention, the isomer mixture of hexyl alcohol of the plasticizer composition includes two or more selected from the group consisting of 1-hexanol, 1-methylpentanol, 2-methylpentanol, 3-methylpentanol, 4-methylpentanol, 1,1-dimethylbutanol, 1,2-dimethylbutanol, 1,3-dimethylbutanol, 2,2-dimethylbutanol, 2,3-dimethylbutanol, 3,3-dimethylbutanol, 1-ethylbutanol, 2-ethylbutanol, 3-ethylbutanol and cyclopentyl methanol.

According to the alcohols included in such hexyl alcohol isomers, the alkyl groups of R1 to R3 of Formula 1 may be determined, and in a final composition, various compositions in which three, two or one of the isomer alkyl groups of hexyl alcohol are bonded as three alkyl groups may be included, and the ratio of components in the final composition may be determined according to the component ratio of alcohols reacted.

As described above, in the application of a cyclohexane triester-based plasticizer, if an alcohol having 6 carbon atoms is used, suitable level of absorption rate could be secured when compared with an alcohol having less than 6 carbon atoms, and processability improvement may be achieved, tensile strength, elongation rate, volatile loss and migration loss may be markedly improved, and plasticization efficiency may be better when compared with an alcohol having more than 6 carbon atoms.

In addition, since there is no unsaturated bond in a central core moiety, marked improvement of light resistance may be expected when compared with a trimellitate-based plasticizer which has a benzene ring including an unsaturated bond as a core moiety.

In the plasticizer composition according to an embodiment of the present invention, an alcohol of a mixture of isomers is applied, and contrary to theoretical prediction, improved effects of tensile strength, plasticization efficiency and volatile loss could be obtained when compared with a case including only a linear hexyl alcohol.

The isomer mixture of hexyl alcohol of the plasticizer composition according to an embodiment of the present invention has the degree of branching of less than 2.0, preferably, 1.5 or less. Particularly, the degree of branching may be 1.5 or less, 1.3 or less, more preferably, 1.1 or less. In addition, the degree of branching may be 0.1 or more, 0.2 or more, 0.3 or more, most preferably, 0.7 or more. The degree of branching of the isomer mixture of hexyl alcohol may be maintained even after being transformed into a cyclohexane triester-based plasticizer composition. If the degree of branching is greater than 2.0, balance between physical properties may be broken, and defects falling short of one or more evaluation levels of a product may arise, but within preferable range of 1.5 or less, the improvement of migration loss and volatile loss as well as mechanical properties may be optimized, and balance between physical properties may be excellent.

Here, the degree of branching may mean that how many branch carbon atoms do the alkyl groups bonded to a material included in the composition have, and may be determined according to the weight ratio of the corresponding material. For example, if 60 wt % of n-hexyl alcohol, 30 wt % of methylpentyl alcohol and 10 wt % of ethylbutyl alcohol are included in an alcohol mixture, the branch carbon numbers of the alcohols are 0, 1 and 2, respectively, and the degree of branching may be calculated by [(60×0)+(30×1)+(10×2)]/100, and may be 0.5. Here, the branch carbon number of cyclopentyl methanol is regarded 0.

The plasticizer composition according to an embodiment of the present invention may include 1-hexanol, 2-methylpentanol and 3-methylpentanol in an isomer mixture of hexyl alcohol. Theoretically, a case of including only 1-hexanol is expected to have excellent linearity and show the best effects, but a case of including 2-methylpentanol and 3-methylpentanol together is preferable considering the balance of physical properties, and excellent effects could be obtained in view of volatile loss.

The branch type hexyl alcohol including 2-methylpentanol and 3-methylpentanol may be included in 40 parts by weight or more, 50 parts by weight or more, 60 parts by weight or more, preferably, 65 parts by weight or more, 70 parts by weight or more based on 100 parts by weight of the isomer mixture. The amount of the branch type may be the total in the maximum amount, 99 parts by weight or less, 98 parts by weight or less, preferably, 95 parts by weight or less, or 90 parts by weight or less. With the branch type hexyl alcohol in the range, the improvement of mechanical properties may be expected.

In addition, the linear alcohol of 1-hexanol may be included in 50 parts by weight or less, 40 parts by weight or less, preferably, 30 parts by less based on 100 parts by weight of the isomer mixture. The 1-hexanol may not be present in the component but may be included at least 2 parts by weight or more, and in this case, advantages of maintaining the balance between physical properties and improving mechanical properties may be obtained. Theoretically, linear alcohols are known to show excellent effects, but in the present invention, different results from the theoretical results were obtained, and better balance of physical properties was obtained if an isomer mixture including a branch type alcohol was applied.

The plasticizer composition according to an embodiment of the present invention may include 1-hexanol, 2-methylpentanol, 3-methylpentanol and cyclopentylmethanol in the isomer mixture of hexyl alcohol. Preferably, by further including cyclopentylmethanol, volatile loss may be improved while maintaining the balance between physical properties.

In this case, the cyclopentylmethanol may be 20 parts by weight or less, preferably, 15 parts by weight or less, more preferably, 10 parts by weight or less with respect to 100 parts by weight of the isomer mixture, or may not be present, but the minimum amount to obtain effects thereby may be 2 parts by weight.

Particularly, due to the features on the ratio degree of the presence of branch type alkyl groups among total alkyl radicals in a final composition, further, on the ratio degree of the presence of a specific branched alkyl radical among the branch type alkyl groups, plasticization efficiency and the balance of physical properties of migration/loss properties may be controlled, mechanical properties such as tensile strength and elongation rate and stress resistance may be maintained to equal or better levels. In addition, due to the interaction of four types of cyclohexane triesters included in the composition, light resistance may be markedly improved, and this could be achieved from the components of the aforementioned isomers of hexyl alcohol and the component ratios thereof.

Through this, products which may eliminate environmental issues of the conventional phthalate-based products and further improve loss properties may be accomplished, the migration and loss properties of the conventional terephthalate-based products may be markedly improved, and products having greatly improved light resistance and heat resistance when compared with the conventional commercial products may be achieved.

A method of preparing the plasticizer composition according to an embodiment of the present invention is a method well-known in the art, and any methods that may prepare the aforementioned plasticizer composition may be applied without specific limitation.

That is, by suitably combining hydrogenation, direct esterification and transesterification, the plasticizer composition according to the present invention may be prepared. For example, the composition may be prepared by hydrogenating a trimellitate composition which is prepared by the direct esterification reaction of trimellitic acid and an isomer mixture of hexyl alcohol, or the composition may also be prepared by hydrogenating a trimellitate composition prepared by the transesterification of trimellitate and one type of a separated alcohol.

In addition, the order of esterification and hydrogenation may be exchanged. A method of performing direct esterification of cyclohexane tricarboxylic acid as a reactant, which is obtained by hydrogenating trimellitic acid prior to performing esterification, with an isomer mixture of hexyl alcohol may be applied, or a method of performing transesterification of cyclohexane triester as a reactant, which is obtained by hydrogenating trimellitate prior to performing esterification, with one or more types of separated alcohols.

The plasticizer composition according to an embodiment of the present invention is a material prepared by suitably combining the esterification and hydrogenation, and any preparation methods satisfying the aforementioned conditions may be applied without specific limitation.

For example, the direct esterification may be performed through a step of injecting trimellitic acid or cyclohexane tricarboxylic acid or derivatives thereof (ex. anhydride), and an isomer mixture of hexyl alcohol, adding a catalyst and reacting under a nitrogen atmosphere; a step of removing unreacted alcohol and neutralizing unreacted acid; and a step of dehydrating by distillation under a reduced pressure and filtering.

The components of the isomer mixture of hexyl alcohol and the weight ratios of the components are the same as described above. The alcohol may be used in a range of 150 to 500 mol %, 200 to 400 mol %, 200 to 350 mol %, 250 to 400 mol %, or 270 to 330 mol % based on 100 mol % of the trimellitic acid or the cyclohexane tricarboxylic acid, and by controlling the amount of the alcohol, the component ratios in a final composition may be controlled.

The catalyst may be, for example, at least one or more selected from an acid catalyst such as sulfuric acid, hydrochloric acid, phosphoric acid, nitric acid, paratoluenesulfonic acid, methanesulfonic acid, ethanesulfonic acid, propanesulfonic acid, butanesulfonic acid, and alkyl sulfate, a metal salt such as aluminum lactate, lithium fluoride, potassium chloride, cesium chloride, calcium chloride, iron chloride, and aluminum phosphate, a metal oxide such as a heteropoly acid, natural/synthetic zeolites, cation and anion exchange resins, and an organometal such as tetraalkyl titanate and polymers thereof. In a particular embodiment, the catalyst may use tetraalkyl titanate. Preferably, as an acid catalyst having a low activation temperature, paratoluenesulfonic acid and methanesulfonic acid may be suitable.

The amount used of the catalyst may be different according to the types thereof, and for example, a homogeneous catalyst may be used in an amount of 0.01 to 5 wt %, 0.01 to 3 wt %, 1 to 5 wt % or 2 to 4 wt % based on total 100 wt % of reactants, and a heterogeneous catalyst may be used in an amount of 5 to 200 wt %, 5 to 100 wt %, 20 to 200 wt %, or 20 to 150 wt % based on the total amount of the reactants.

In this case, the reaction temperature may be within a range of 180 to 280° C., 200 to 250° C., or 210 to 230° C.

In another embodiment, the transesterification may be reaction of a trimellitate (may be a cyclohexane triester if hydrogenation is performed first, and hereinafter, description will be given with trimellitate) and an alcohol having an alkyl radical different from the alkyl radical of the trimellitate (linear alcohol if the trimellitate is combined with a branch type alkyl group, and branch type alcohol if the trimellitate is combined with a linear alkyl group). Here, the alkyl groups of the trimellitate and the alcohol may be exchanged.

The "transesterification" used in the present invention means the reaction of an alcohol and an ester as shown in Reaction 1 below to exchange R" of the ester with R' of the alcohol as shown in the following Reaction 1:

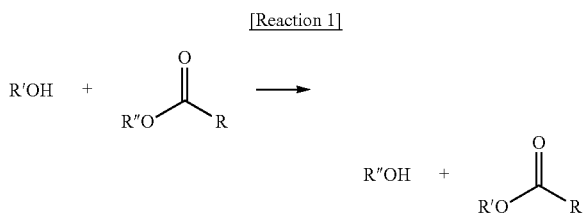

Generally, if the transesterification is carried out, and alkyl groups are two types, four types of ester compositions may be produced according to four cases as follows: a case where the alkoxide of an alcohol attacks three carbon atoms of an ester group (RCOOR") which is present in an ester compound; a case where the alkoxide of an alcohol attacks two carbon atoms of an ester group (RCOOR") which is present in an ester compound; a case where the alkoxide of an alcohol attacks one carbon atom of an ester group (RCOOR") which is present in an ester compound; and a unreacted case wherein no reaction is performed.

However, in case of the cyclohexane triester included in the plasticizer composition according to the present invention, for a case of exchanging two ester groups and a case of exchanging one ester group according to the bonding positions of ester groups, three types may be formed, respectively. Accordingly, at most 8 types of compounds may be mixed in a final composition. However, in the isomer mixture of hexyl alcohol according to the present invention, two or more types of alkyl groups are present, and the types may be more diverse.

The composition ratio of the mixture prepared through the transesterification may be controlled according to the addition amount of the alcohol. The amount added of the alcohol may be 0.1 to 89.9 parts by weight, particularly, 3 to 50 parts by weight, more particularly, 5 to 40 parts by weight based on 100 parts by weight of the trimellitate compound. For reference, the factor determining the component ratios in a final composition may be the amount added of an alcohol as in the direct esterification.

In regard of the trimellitate compound, since the mole fraction of the trimellitate which participates in the transesterification may increase according to the increase of the amount added of the alcohol, the amount of the trimellitate which is a product in the mixture may increase, and correspondingly, the amount of the trimellitate which is present in an unreacted state, may tend to decrease.

According to an embodiment of the present invention, the molar ratio of the reactants, trimellitate and alcohol may be, for example, 1:0.005 to 5.0, 1:0.05 to 2.5, or 1:0.1 to 1.0, and within this range, processability and economic feasibility may be excellent, and a plasticizer composition capable of achieving the above-described effects may be obtained.

According to an embodiment of the present invention, the transesterification may be performed at a reaction temperature of 120° C. to 190° C., preferably, 135° C. to 180° C., more preferably, 141° C. to 179° C. for 10 minutes to 10 hours, preferably, 30 minutes to 8 hours, more preferably, 1 to 6 hours. Within the temperature and time ranges, the component ratio of a final plasticizer composition may be efficiently controlled. In this case, the reaction time may be calculated from a point when the reaction temperature is achieved after elevating the temperature of the reactants.

The transesterification may be performed under an acid catalyst or a metal catalyst, and in this case, effects of decreasing the reaction time may be achieved.

The acid catalyst may include, for example, sulfuric acid, methanesulfonic acid or p-toluenesulfonic acid, and the metal catalyst may include, for example, an organometal catalyst, a metal oxide catalyst, a metal salt catalyst, or a metal itself.

The metal component may be, for example, any one selected from the group consisting of tin, titanium and zirconium, or a mixture of two or more thereof.

In addition, a step of removing unreacted alcohol and reaction by-products by distillation may be further included after performing the transesterification. The distillation may be, for example, a two-step distillation by which the alcohol and the by-products are individually separated using the difference of the boiling points. In another embodiment, the distillation may be mixed distillation. In this case, effects of relatively stable securing of the desired composition ratio of an ester-based plasticizer composition may be achieved. The mixed distillation means distillation of the unreacted alcohol and the by-products simultaneously.

The hydrogenation step may be reaction for removing the aromaticity of the benzene ring of the trimellitate by adding hydrogen in the presence of a metal catalyst and may be a kind of reduction reaction.

The hydrogenation is for synthesizing a cyclohexane triester or cyclohexane tricarboxylic acid by reacting the trimellitate and hydrogen in the presence of a metal catalyst, and the reaction conditions may include all common reaction conditions which may be applied to hydrogenate only a benzene ring without affecting a carbonyl group (ester or carboxylic acid) which is substituted at benzene.

The hydrogenation may be performed by further including an organic solvent such as ethanol, without limitation. The metal catalyst may use a Rh/C catalyst, a Pt catalyst, a Pd catalyst, etc., commonly used for hydrogenating a benzene ring, but any one capable of undergoing the above-described hydrogenation may be used without limitation.

In the plasticizer composition according to an embodiment of the present invention, direct esterification may be applied. Among the alcohols applied in the direct esterification, by applying a mixture of alcohols having linear and branch type alkyls as an alcohol composition, the component ratio of cyclohexane triester finally prepared may be controlled, and the molar ratio of the branch type alkyl group among total alkyl radicals and the molar ratio of a specific branch type alkyl group among the branch type alkyl radicals may be controlled.

As described above, relating to the method of preparing the plasticizer composition according to an embodiment of an embodiment of the present invention, esterification and hydrogenation have been explained, but in the hydrogenation, a relatively expensive catalyst metal is used, and reaction conditions are severe, and the unit cost may be increased. Accordingly, the preparation is preferably performed through esterification using a hydrogenated raw material, if possible.

According to another embodiment of the present invention, a resin composition including the plasticizer composition and a resin is provided.

The resin may use resins well-known in the art. For example, a mixture of one or more selected from the group consisting of a straight vinyl chloride polymer, a paste vinyl chloride polymer, an ethylene vinyl acetate copolymer, an ethylene polymer, a propylene polymer, polyketone, polystyrene, polyurethane, natural rubber, synthetic rubber and thermoplastic elastomer may be used, without limitation.

The plasticizer composition may be included in 5 to 150 parts by weight, preferably, 5 to 130 parts by weight, or 10 to 120 parts by weight based on 100 parts by weight of the resin.

Generally, the resin using the plasticizer composition may be prepared into a resin product through a melt processing or a plastisol processing, and a resin by the melt processing and a resin from the plastisol processing may be produced differently according to each polymerization method.

For example, in case of using a vinyl chloride polymer in a melt processing, solid phase resin particles having a large average particle diameter are prepared by suspension polymerization, or the like and used, and the vinyl chloride polymer is referred to as a straight vinyl chloride polymer. In case of using a vinyl chloride polymer in a plastisol processing, a sol state resin as minute resin particles are prepared by emulsion polymerization, or the like and used, and this vinyl chloride polymer is referred to as a paste vinyl chloride resin.

In case of the straight vinyl chloride polymer, a plasticizer may be included in a range of 5 to 80 parts by weight with respect to 100 parts by weight of the polymer, and in case of the paste vinyl chloride polymer, the plasticizer may be included in a range of 40 to 120 parts by weight with respect to 100 parts by weight of the polymer.

The resin composition may further include a filler. The filler may be 0 to 300 parts by weight, preferably, 50 to 200 parts by weight, more preferably, 100 to 200 parts by weight based on 100 parts by weight of the resin.

The filler may use fillers well-known in the art and is not specifically limited. For example, the filler may be a mixture of one or more kinds selected from silica, magnesium carbonate, calcium carbonate, hard coal, talc, magnesium hydroxide, titanium dioxide, magnesium oxide, calcium hydroxide, aluminum hydroxide, aluminum silicate, magnesium silicate and barium sulfate.

In addition, the resin composition may further include other additives such as a stabilizer as necessary. Each of the other additives such as the stabilizer may be, for example, 0 to 20 parts by weight, preferably, 1 to 15 parts by weight based on 100 parts by weight of the resin.

The stabilizer may use, for example, a calcium-zinc-based (Ca—Zn-based) stabilizer such as a composite stearate of calcium-zinc or a barium-zinc-based (Ba—Zn-based) stabilizer, but is not specifically limited.

The resin composition may be applied to both a melt processing and a plastisol processing as described above, and a calendaring processing, an extrusion processing, or an injection processing may be applied to the melt processing, and a coating processing, or the like may be applied to the plastisol processing.

EXAMPLES

Hereinafter, embodiments will be explained in detail to particularly explain the present invention. The present invention may, however, be embodied in different forms and should not be construed as limited to the embodiments set forth herein. Rather, these embodiments are provided so that this disclosure will be thorough and complete, and will fully convey the scope of the inventive concept to those skilled in the art.

Example 1

To a reactor equipped with a stirrer, a condenser and a decanter, 595 g of cyclohexane 1,2,4-tricarboxylic anhydride, 1,195 g of an isomer mixture of hexyl alcohol, and 2 g of tetrabutyl titanate (TnBT) were injected, and esterification was carried out under a nitrogen atmosphere. After finishing the reaction, the catalyst and product were neutralized with an aqueous alkaline solution, and unreacted alcohol and moisture were separated to finally obtain a plasticizer composition.

Here, the alcohol composition of the isomer mixture of hexyl alcohol is shown in Table 1 below.

Examples 2 to 12

Plasticizer compositions were obtained by the same method as in Example 1 except for changing alcohol compositions of the isomer mixture of hexyl alcohol as described in Table 1 in Example 1.

TABLE 1

| | 1-hexanol | 2-methyl-pentanol | 3-methyl-pentanol | 2-ethyl-butanol | Cyclopentyl methanol |
|---|---|---|---|---|---|
| Example 1 | 30 | 15 | 50 | — | 5 |
| Example 2 | 30 | 30 | 30 | — | 10 |
| Example 3 | 10 | 40 | 40 | — | 10 |
| Example 4 | 20 | 30 | 40 | — | 5 |
| Example 5 | 5 | 30 | 50 | — | 15 |
| Example 6 | 2 | 50 | 40 | — | 8 |
| Example 7 | 8 | 60 | 30 | — | 2 |
| Example 8 | 10 | 40 | 50 | — | — |
| Example 9 | 30 | 30 | 40 | — | — |
| Example 10 | — | 40 | 50 | — | 10 |
| Example 11 | 10 | — | 80 | — | 10 |
| Example 12 | 30 | — | — | 70 | — |

* The contents of the alcohols are all parts by weight. The component contents in the isomer mixture of hexyl alcohol were measured by gas chromatography and analyzed by a gas chromatography equipment of Agilent Co. (product name: Agilent 7890 GC, column: HP-5, carrier gas: helium (flow rate of 2.4 ml/min), detector: F.I.D., injection volume: 1 μl, initial value: 70° C./4.2 min, end value: 280° C./7.8 min, program rate: 15° C./min).

Comparative Example 1

Diisononyl phthalate (DINP), a product of LG Chem, was used as a plasticizer composition.

Comparative Example 2

Di(2-ethylhexyl) terephthalate (DEHTP, LGflex GL300), a product of LG Chem, was used as a plasticizer composition.

Comparative Example 3

A plasticizer composition was obtained by the same method as in Example 1 except for using trimellitic acid instead of the cyclohexane 1,2,4-tricarboxylic anhydride, and using a branch type pentanol (100% of branch type 2-methylbutanol) instead of the isomer mixture of hexyl alcohol in Example 1.

Comparative Example 4

A plasticizer composition was obtained by the same method as in Example 1 except for using trimellitic acid instead of the cyclohexane 1,2,4-tricarboxylic anhydride, and using an isomer mixture of pentanol (a weight ratio of n-pentanol and 2-methylbutalol of 5:5) instead of the isomer mixture of hexyl alcohol in Example 1.

Comparative Example 5

A plasticizer composition was obtained by the same method as in Example 1 except for using trimellitic acid instead of the cyclohexane 1,2,4-tricarboxylic anhydride, and using an isomer mixture of hexyl alcohol (a weight ratio of n-hexanol and 2-ethylbutalol of 7:3) in Example 1.

Comparative Example 6

A plasticizer composition was obtained by the same method as in Example 1 except for using isobutanol instead of the isomer mixture of hexyl alcohol in Example 1.

Comparative Example 7

A plasticizer composition was obtained by the same method as in Example 1 except for using n-butanol instead of the isomer mixture of hexyl alcohol in Example 1.

Comparative Example 8

A plasticizer composition was obtained by the same method as in Example 1 except for using branch type pentanol (100% of branch type 2-methylbutanol) instead of the isomer mixture of hexyl alcohol in Example 1.

Comparative Example 9

A plasticizer composition was obtained by the same method as in Example 1 except for using n-pentanol instead of the isomer mixture of hexyl alcohol in Example 1.

Comparative Example 10

A plasticizer composition was obtained by the same method as in Example 1 except for using n-heptanol instead of the isomer mixture of hexyl alcohol in Example 1.

Comparative Example 11

A plasticizer composition was obtained by the same method as in Example 1 except for using n-hexanol instead of the isomer mixture of hexyl alcohol in Example 1.

Comparative Example 12

A plasticizer composition was obtained by the same method as in Example 1 except for using 2-ethylbutanol instead of the isomer mixture of hexyl alcohol in Example 1.

Experimental Example 1: Performance Evaluation of Calendaring Sheet

By using the plasticizers of the Examples and Comparative Examples, specimens were manufactured according to ASTM D638 and the prescription and manufacturing conditions below.

(1) Prescription:
  100 parts by weight of a straight vinyl chloride polymer (LS100S), 40 parts by weight of a plasticizer and 3 parts by weight of a stabilizer (BZ-153T)
(2) Mixing: mixing at 98° C. in 700 rpm
(3) Manufacture of Specimen: 1T and 3T sheets were manufactured by processing at 160° C. for 4 minutes by a roll mill, and at 180° C. for 2.5 minutes (low pressure) and 2 minutes (high pressure) by a press.
(4) Test Items
1) Hardness: Shore hardness (Shore "A") at 25° C. was measured using a 3T specimen for 10 seconds using ASTM D2240. The plasticization efficiency was assessed excellent if the value was small.
2) Tensile Strength: By an ASTM D638 method, a specimen was drawn in a cross-head speed of 200 mm/min using a test apparatus of U.T.M (manufacturer: Instron, model name: 4466), and a point where the 1T specimen was cut was measured. The tensile strength was calculated as follows.

Tensile strength (kgf/cm$^2$)=load value (kgf)/thickness (cm)×width (cm)

3) Elongation Rate Measurement: By an ASTM D638 method, a specimen was drawn in a cross-head speed of 200 mm/min using a test apparatus of U.T.M, and a point where the 1T specimen was cut was measured. The elongation rate was calculated as follows.

Elongation rate(%)=length after elongation/initial length×100

4) Migration Loss Measurement: According to KSM-3156, a specimen with a thickness of 2 mm was obtained, glass plates were attached onto both sides of 1T specimen, and a load of 1 kgf/cm$^2$ was applied. The specimen was stood in a hot air circulation type oven (80° C.) for 72 hours and then taken out and cooled at room temperature for 4 hours. Then, the weights of the specimen from which glass plates attached onto both sides thereof were removed, were measured before and after standing the glass plates and the specimen plate in the oven, and the migration loss was calculated as follows.

Migration loss(%)={[(weight of initial specimen)−(weight of specimen after standing in oven)]/(weight of initial specimen)}×100

5) Volatile Loss Measurement: The specimen manufactured was processed at 100° C. for 168 hours, and the weight of the specimen was measured.

Volatile loss (wt %)={[(weight of initial specimen)−(weight of specimen after processing)]/(weight of initial specimen)}×100

6) Stress Test (Stress Resistance): A specimen with a thickness of 2 mm in a bent state was stood at 23° C. for 72 hours, and the degree of migration (degree of oozing) was observed. The results were recorded as numerical values (by 0.5 unit from 0 to 3), and excellent properties were shown if the value was closer to 0.
7) Absorption Rate Measurement
  Absorption rate was evaluated by measuring the time consumed for mixing a resin and an ester compound and stabilizing the torque of a mixer by using a planetary mixer (Brabender, P600) in conditions of 77° C. and 60 rpm.
8) Light Resistance Measurement
  By a method of ASTM 4329-13, the specimen was put on QUV (QUV/se, Q-LAB) and exposed to UV (340 nm) for 400 hours, and color change (ΔE) was confirmed using Reflectometer (Tintometer, LoviBond).

(5) Evaluation Results

The evaluation results on the test items are listed in Table 2 below.

TABLE 2

|  | Hardness (Shore A) | Tensile strength (kgf/cm$^2$) | Elongation rate (%) | Migration loss (%) | Volatile loss (%) | Stress migration | Absorption rate | Light resistance |
|---|---|---|---|---|---|---|---|---|
| Example 1 | 90.5 | 240.2 | 311.0 | 0.42 | 0.65 | 0 | 4 m11 s | 1.02 |
| Example 2 | 90.6 | 234.5 | 308.9 | 0.44 | 0.68 | 0 | 4 m15 s | 1.05 |
| Example 3 | 91.0 | 233.5 | 308.7 | 0.65 | 0.72 | 0 | 4 m35 s | 1.05 |
| Example 4 | 90.8 | 234.0 | 306.5 | 0.50 | 0.66 | 0 | 4 m20 s | 1.10 |
| Example 5 | 91.3 | 232.7 | 305.6 | 0.53 | 0.62 | 0 | 4 m30 s | 1.01 |
| Example 6 | 90.5 | 228.9 | 302.1 | 0.44 | 0.74 | 0 | 4 m25 s | 1.00 |
| Example 7 | 91.1 | 225.6 | 302.8 | 0.64 | 0.75 | 0 | 4 m30 s | 1.05 |
| Example 8 | 91.3 | 237.6 | 309.4 | 0.66 | 1.01 | 0 | 4 m25 s | 1.10 |
| Example 9 | 91.0 | 240.2 | 308.7 | 0.58 | 0.86 | 0 | 4 m20 s | 1.02 |
| Example 10 | 92.2 | 236.5 | 315.4 | 0.66 | 0.88 | 0 | 4 m35 s | 1.08 |
| Example 11 | 92.2 | 237.9 | 314.2 | 0.59 | 1.30 | 0 | 4 m45 s | 1.17 |
| Example 12 | 92.0 | 224.9 | 310.5 | 0.62 | 1.35 | 0 | 4 m30 s | 1.14 |
| Comparative | 93.4 | 234.7 | 319.6 | 2.16 | 3.76 | 0.5 | 5 m38 s | 1.52 |

TABLE 2-continued

| | Hardness (Shore A) | Tensile strength (kgf/cm²) | Elongation rate (%) | Migration loss (%) | Volatile loss (%) | Stress migration | Absorption rate | Light resistance |
|---|---|---|---|---|---|---|---|---|
| Example 1 Comparative Example 2 | 94.9 | 234.0 | 322.1 | 3.43 | 4.42 | 3.0 | 6 m40 s | 4.87 |
| Comparative Example 3 | 92.0 | 220.5 | 288.6 | 0.77 | 1.42 | 0 | 4 m20 s | 4.57 |
| Comparative Example 4 | 92.8 | 221.6 | 290.3 | 1.25 | 2.38 | 0.5 | 4 m10 s | 4.88 |
| Comparative Example 5 | 93.1 | 223.4 | 300.2 | 0.88 | 1.25 | 0.5 | 5 m10 s | 5.21 |
| Comparative Example 6 | 91.7 | 201.6 | 254.5 | 0.49 | 9.84 | 0 | Discharged | 1.32 |
| Comparative Example 7 | 92.4 | 214.7 | 260.6 | 0.38 | 7.88 | 0 | Discharged | 1.28 |
| Comparative Example 8 | 91.2 | 210.4 | 266.9 | 0.56 | 5.26 | 0 | 4 m00 s | 1.10 |
| Comparative Example 9 | 91.4 | 209.7 | 273.7 | 0.35 | 2.82 | 0 | 4 m05 s | 1.09 |
| Comparative Example 10 | 94.0 | 230.2 | 270.3 | 1.45 | 1.01 | 1.0 | 6 m05 s | 1.14 |
| Comparative Example 11 | 92.3 | 220.8 | 305.9 | 0.59 | 1.24 | 0 | 4 m46 s | 1.02 |
| Comparative Example 12 | 94.2 | 220.1 | 298.7 | 1.54 | 2.58 | 1.0 | 5 m15 s | 1.18 |

Referring to the results of Table 2, it could be confirmed that excellent effects of most physical properties were shown, and balance between physical properties, particularly, tensile strength, volatile loss, migration loss and light resistance were excellent in cases of applying the plasticizers of Examples 1 to 12 when compared with cases of applying the plasticizers of Comparative Examples 1 to 12. Further, the absorption rate was 4 minutes or so and was not so fast, and there were no worries on discharge, and in addition, the absorption rate was not greater than 5 minutes, and processability was also excellent. Particularly, it could be confirmed that migration loss and volatile loss were markedly improved when compared with Comparative Examples 1 and 2, which applied the conventional commercial plasticizers, absorption rate also was improved, and the improvement of processability could be expected, and stress resistance and light resistance were very excellent when compared with Comparative Example 2 which corresponded to the conventional eco-friendly product.

In addition, if all central core moieties were saturated as in the plasticizer composition according to the present invention, it could be confirmed that effects of markedly improved light resistance were achieved, and improved elongation rate and tensile strength were achieved when compared with Comparative Examples 3 to 5, in which an unsaturated benzene ring was present.

In addition, it could be confirmed that in case where alcohols having 4 carbon atoms were applied as in Comparative Examples 6 and 7, plasticizers were not normally absorbed during blending, processability was very poor to such an extent that the measurement of absorption rate was impossible due to repeated agglomeration and release and the repeated absorption and discharge, and mechanical properties and volatile loss were degrees not satisfying basic conditions required by a consumer. It was found that Comparative Examples 8 and 9 in which alcohols having 5 carbon atoms were applied showed very inferior mechanical properties of tensile strength and elongation rate and significantly inferior volatile loss as in a case of having 4 carbon atoms. Also, Comparative Example 10 with 7 carbon atoms showed very inferior elongation rate and inferior stress resistance.

Further, it was confirmed that Comparative Example 11 in which only 1-hexanol was applied was expected to show excellent effects though an alcohol having 6 carbon atoms was applied, but an isomer mixture was not applied, and showed lower degree of most physical properties, particularly, inferior tensile strength, volatile loss and plasticization efficiency (hardness) when compared with the Examples in which isomer mixtures were applied. Also, in Comparative Example 12 in which branch type 2-ethylbutanol was solely applied, slow absorption rate was stood out, and all physical properties such as migration loss, volatile loss and tensile strength were inferior.

The invention claimed is:

1. A cyclohexane triester-based plasticizer composition, comprising:
   a cyclohexane triester-based composition comprising one or more cyclohexane triesters of Formula 1,
   wherein alkyl groups of the cyclohexane triester are derived from an isomer mixture of hexyl alcohol having a degree of branching of 2.0 or less, and
   wherein the isomer mixture of hexyl alcohol comprises two or more alcohols selected from the group consisting of 1-hexanol, 1-methylpentanol, 2-methylpentanol, 3-methylpentanol, 4-methylpentanol, 1,1-dimethylbutanol, 1,2- dimethylbutanol, 1,3-dimethylbutanol, 2,2-dimethylbutanol, 2,3-dimethylbutanol, 3,3-dimethylbutanol, 1-ethylbutanol, 2-ethylbutanol, 3-ethylbutanol and cyclopentyl methanol:

[Formula 1]

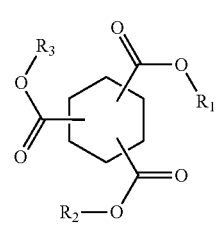

wherein, in Formula 1,

R₁ to R₃ are each independently an n-hexyl group, a branch type hexyl group or a cyclopentyl methyl group.

2. The plasticizer composition according to claim 1, wherein the isomer mixture of hexyl alcohol has the degree of branching of 1.5 or less.

3. The plasticizer composition according to claim 1, wherein the isomer mixture of hexyl alcohol comprises 1-hexanol, 2-methylpentanol and 3-methylpentanol.

4. The plasticizer composition according to claim 1, wherein the isomer mixture of hexyl alcohol comprises 40 parts by weight or more of a branch type alcohol with respect to 100 parts by weight of the isomer mixture.

5. The plasticizer composition according to claim 1, wherein the isomer mixture of hexyl alcohol comprises 50 to 95 parts by weight of a branch type alcohol with respect to 100 parts by weight of the isomer mixture.

6. The plasticizer composition according to claim 1, wherein the isomer mixture of hexyl alcohol comprises 40 parts by weight or less of 1-hexanol with respect to 100 parts by weight of the isomer mixture.

7. The plasticizer composition according to claim 1, wherein the isomer mixture of hexyl alcohol comprises 1-hexanol, 2-methylpentanol, 3-methylpentanol and cyclopentylmethanol.

8. The plasticizer composition according to claim 7, wherein the isomer mixture of hexyl alcohol comprises 20 parts by weight or less of the cyclopentylmethanol with respect to 100 parts by weight of the isomer mixture.

9. A resin composition, comprising:
100 parts by weight of a resin; and 5 to 150 parts by weight of the plasticizer composition according to claim 1.

10. The resin composition according to claim 9, wherein the resin is one or more selected from the group consisting of a straight vinyl chloride polymer, a paste vinyl chloride polymer, an ethylene vinyl acetate copolymer, an ethylene polymer, a propylene polymer, polyketone, polystyrene, polyurethane, natural rubber, synthetic rubber and thermoplastic elastomer.

* * * * *